(12) United States Patent
Beck et al.

(10) Patent No.: US 10,596,011 B2
(45) Date of Patent: Mar. 24, 2020

(54) ORTHOPAEDIC SURGICAL INSTRUMENT AND METHOD FOR POSITIONING AN ACETABULAR PROSTHETIC COMPONENT

(71) Applicant: DePuy Ireland Unlimited Company, Ringaskiddy, Cork County, OT (IE)

(72) Inventors: Clinton Beck, Warsaw, IN (US); Larry McCleary, Warsaw, IN (US)

(73) Assignee: DePuy Ireland Unlimited Company, Ringaskiddy, Co Cork (IE)

( * ) Notice: Subject to any disclaimer, the term of this patent is extended or adjusted under 35 U.S.C. 154(b) by 228 days.

(21) Appl. No.: 15/885,032

(22) Filed: Jan. 31, 2018

(65) Prior Publication Data

US 2019/0231558 A1 Aug. 1, 2019

(51) Int. Cl.
*A61F 2/46* (2006.01)
*A61F 2/30* (2006.01)

(52) U.S. Cl.
CPC .......... *A61F 2/4603* (2013.01); *A61F 2/4607* (2013.01); *A61F 2/4609* (2013.01); *A61F 2/4684* (2013.01); *A61F 2002/30537* (2013.01); *A61F 2002/4623* (2013.01); *A61F 2002/4625* (2013.01)

(58) Field of Classification Search
CPC ..... A61F 2/4609; A61F 2/4607; A61F 2/4603
See application file for complete search history.

(56) References Cited

U.S. PATENT DOCUMENTS

| 5,108,448 | A | 4/1992 | Gautier |
| 5,116,339 | A | 5/1992 | Glock |
| 5,171,243 | A | 12/1992 | Kashuba et al. |
| 5,282,864 | A * | 2/1994 | Noiles ............ A61F 2/30721 623/23.43 |
| 5,417,696 | A | 5/1995 | Kashuba et al. |
| 5,507,748 | A | 4/1996 | Sheehan et al. |
| 5,683,399 | A | 11/1997 | Jones |
| 5,928,287 | A | 7/1999 | Keller |
| 5,954,727 | A | 9/1999 | Collazo |
| 6,022,357 | A | 2/2000 | Reu et al. |
| 6,045,583 | A | 4/2000 | Gross et al. |
| 6,063,124 | A * | 5/2000 | Amstutz ............ A61F 2/34 623/22.21 |
| 6,352,559 | B1 | 3/2002 | Church |
| 6,468,281 | B1 | 10/2002 | Badorf et al. |
| 7,037,310 | B2 | 5/2006 | Murphy |
| 7,931,656 | B2 | 4/2011 | Parry et al. |
| 8,277,457 | B1 * | 10/2012 | Burgi ............ A61F 2/4609 606/81 |

(Continued)

FOREIGN PATENT DOCUMENTS

| CN | 103167838 A | 6/2013 |
| DE | 19704577 A1 | 8/1998 |

(Continued)

*Primary Examiner* — Christian A Sevilla
(74) *Attorney, Agent, or Firm* — Barnes & Thornburg LLP

(57) ABSTRACT

An orthopaedic surgical instrument is disclosed. The instrument includes an impactor head and a suction cup coupled to the impactor head. The suction cup including a distal opening that is defined by an outer rim positioned proximal of the impaction surface of the impactor head. The suction cup is configured to engage the orthopaedic prosthetic component to couple the impactor head to the orthopaedic prosthetic component.

6 Claims, 9 Drawing Sheets

(56) References Cited

U.S. PATENT DOCUMENTS

| | | |
|---|---|---|
| 8,535,324 B2 | 9/2013 | Aux Epaules et al. |
| 8,956,366 B2 | 2/2015 | Aux Epaules et al. |
| 9,028,502 B2 | 5/2015 | Burgi |
| 10,405,991 B2 | 9/2019 | Bailey |
| 10,449,061 B2 * | 10/2019 | Slade .................... A61B 17/92 |
| 2002/0107573 A1 * | 8/2002 | Steinberg ......... A61B 17/00234 623/17.12 |
| 2004/0215200 A1 | 10/2004 | Tornier et al. |
| 2005/0137603 A1 * | 6/2005 | Belew .................. A61F 2/4609 606/91 |
| 2005/0149047 A1 | 7/2005 | Parry et al. |
| 2005/0209597 A1 | 9/2005 | Long et al. |
| 2005/0228394 A1 | 10/2005 | Bihary et al. |
| 2006/0149285 A1 | 7/2006 | Burgi et al. |
| 2006/0167462 A1 | 7/2006 | Raugel et al. |
| 2006/0229630 A1 | 10/2006 | Collins et al. |
| 2009/0216240 A1 * | 8/2009 | Posdal .................. A61F 2/4609 606/99 |
| 2009/0234453 A1 * | 9/2009 | Steinberg ........... A61B 17/1617 623/16.11 |
| 2009/0248027 A1 | 10/2009 | Imhof et al. |
| 2009/0281550 A1 | 11/2009 | Keller |
| 2011/0082462 A1 * | 4/2011 | Suarez .................. A61B 34/20 606/99 |
| 2011/0288649 A1 * | 11/2011 | Ratzel .................. A61F 2/4637 623/22.24 |
| 2011/0301654 A1 | 12/2011 | Wozencroft et al. |
| 2012/0029524 A1 * | 2/2012 | Imhof-Rothlin ...... A61F 2/4609 606/99 |
| 2012/0059383 A1 * | 3/2012 | Murphy ................ A61F 2/4612 606/99 |
| 2013/0079785 A1 | 3/2013 | Burgi |
| 2014/0228854 A1 * | 8/2014 | Witt .................... A61B 17/1746 606/96 |
| 2015/0094728 A1 | 4/2015 | Rhoades et al. |
| 2015/0305891 A1 * | 10/2015 | Bergin ............... A61B 17/1746 606/91 |
| 2016/0228262 A1 | 8/2016 | Bailey |
| 2017/0020687 A1 | 1/2017 | Rhoades et al. |
| 2018/0280157 A1 | 10/2018 | Schmit |
| 2019/0231558 A1 * | 8/2019 | Beck ..................... A61F 2/4609 |

FOREIGN PATENT DOCUMENTS

| | | | |
|---|---|---|---|
| DE | 19722923 A1 | 8/1998 | |
| DE | 10128234 A1 | 1/2003 | |
| DE | 10250390 A1 | 5/2004 | |
| DE | 102008049661 A1 | 4/2010 | |
| EP | 0811360 A2 | 12/1997 | |
| EP | 2347736 A1 | 7/2011 | |
| FR | 2797180 A1 | 2/2001 | |
| FR | 2809305 A1 | 11/2001 | |
| FR | 2877210 A1 * | 5/2006 | ........... A61F 2/4609 |
| FR | 2877210 A1 | 5/2006 | |
| FR | 2917288 A1 | 12/2008 | |
| GB | 2299758 A | 10/1996 | |
| GB | 2473610 A | 3/2011 | |
| WO | 2008099242 A1 | 8/2008 | |

\* cited by examiner

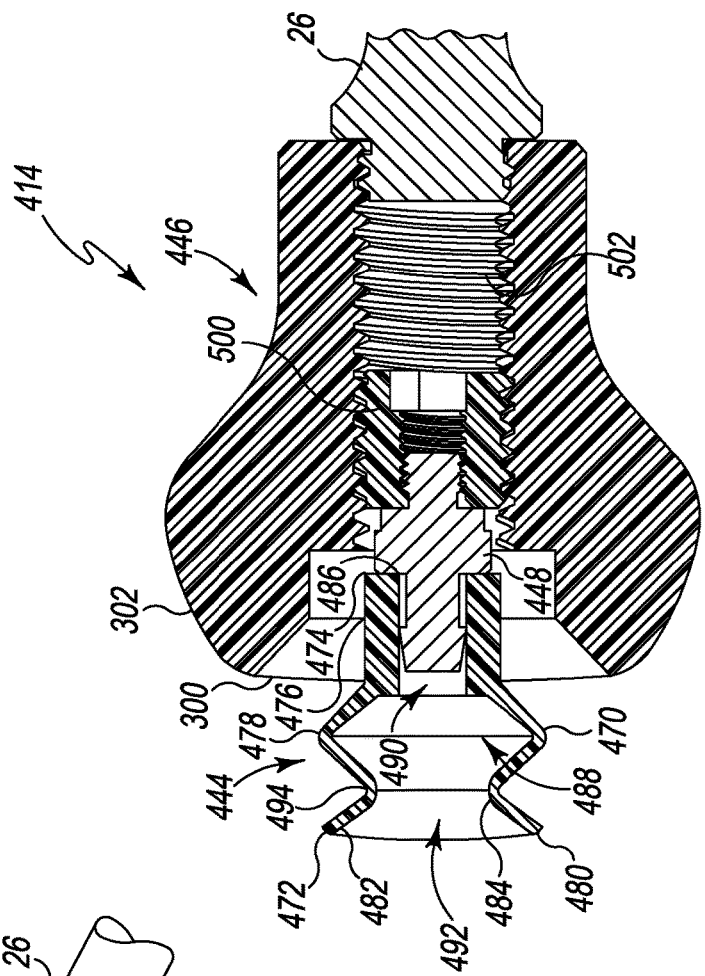
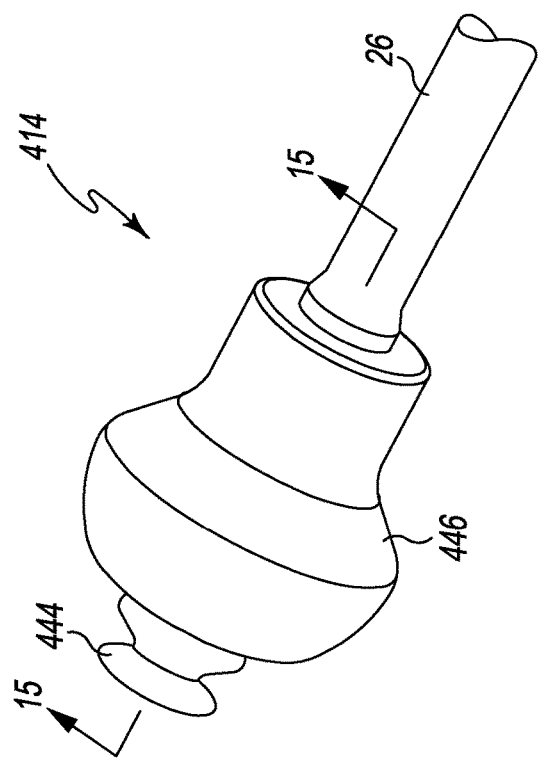
Fig. 14
Fig. 15

ORTHOPAEDIC SURGICAL INSTRUMENT AND METHOD FOR POSITIONING AN ACETABULAR PROSTHETIC COMPONENT

TECHNICAL FIELD

The present disclosure relates generally to orthopaedic surgical instruments and, more particularly, to surgical instruments used to trial and install an acetabular prosthetic component.

BACKGROUND

Joint arthroplasty is a well-known surgical procedure by which a diseased and/or damaged natural joint is replaced by a prosthetic joint. For example, in a hip arthroplasty surgical procedure, a patient's natural hip ball and socket joint is partially or totally replaced by a prosthetic hip joint. A typical prosthetic hip joint includes an acetabular prosthetic component and a femoral head prosthetic component. An acetabular prosthetic component generally includes an outer shell configured to engage the acetabulum of the patient and an inner bearing or liner coupled to the shell and configured to engage the femoral head. The femoral head prosthetic component and inner liner of the acetabular component form a ball and socket joint that approximates the natural hip joint.

To facilitate the replacement of the natural joint with a prosthetic hip joint, orthopaedic surgeons may use a variety of orthopaedic surgical instruments such as, for example, reamers, drill guides, drills, positioners, and/or other surgical instruments.

SUMMARY

According to one aspect, an orthopaedic surgical instrument is disclosed. The orthopaedic surgical instrument comprises an impactor head extending from a distal end to a proximal tip that includes an impaction surface at the proximal tip that is configured to engage an orthopaedic prosthetic component. The orthopaedic surgical instrument also comprises a suction cup coupled to the impactor head. The suction cup has a distal opening that is defined by an outer rim positioned proximal of the impaction surface. The suction cup is configured to engage the orthopaedic prosthetic component to couple the impactor head to the orthopaedic prosthetic component.

In some embodiments, the suction cup may include an inner wall that extends distally from the proximal opening to define a cavity, and the proximal tip of the impactor head may be positioned in the cavity of the suction cup. Additionally, in some embodiments, the inner wall may define at least one corrugation.

In some embodiments, the suction cup may include an outer body that extends from the outer rim to a distal end, and the outer body surrounds the impactor head. Additionally, in some embodiments, the impactor head may be removably coupled to the outer body.

In some embodiments, the impactor head may be one of a plurality of impactor heads configured to be selectively coupled to the suction cup. The plurality of impactor heads may include a first impactor head having a convex curved impaction surface configured to engage the concave curved bearing surface of an acetabular cup prosthesis, and a second impactor head having a concave curved impaction surface configured to engage the convex curved surface of a femoral head prosthesis.

In some embodiments, the orthopaedic surgical instrument may further comprise an elongated body that is coupled to the impaction head and the suction cup. The elongated body may include a handle configured to be gripped by a user and an impaction plate. Additionally, in some embodiments, the elongated body may be removably coupled to the impaction head and the suction cup.

In some embodiments, the impactor head may include an opening that is defined in the proximal tip, and the suction cup may extend outwardly from the opening in the proximal tip. The suction cup may include a shaft extending outwardly from the opening in the proximal tip of the impactor head. An annular flange may extend from the shaft to the outer rim.

In some embodiments, the impactor head may have a central passageway that extends proximally from the opening in the proximal tip. The central passageway may include a distal section that is defined by a tapered surface extending inwardly from the opening in the proximal tip.

In some embodiments, the orthopaedic surgical instrument may further comprise an elongated body that is retained in the central passageway of the impactor head. The elongated body may have a distal end that is coupled to the shaft of the suction cup.

In some embodiments, the elongated body and the suction cup may be movable along a longitudinal axis of the central passageway between a first position in which a first distance along the longitudinal axis is defined between the proximal tip of the impactor head and the outer rim of the suction cup and a second position in which a second distance along the longitudinal axis is defined between the proximal tip of the impactor head and the outer rim of the suction cup. The second distance may be less than the first distance.

In some embodiments, the orthopaedic surgical instrument may further comprise a biasing element positioned between a portion of the elongated body and an inner wall of the impactor head to bias in the first position.

In some embodiments, the impaction surface of the impactor head may be an convex annular outer surface that is configured to engage with a concave inner surface of an acetabular cup prosthesis. Additionally, in some embodiments, the impaction surface may be a first impaction surface, and the impactor head may include a second impaction surface that is a concave inner surface configured to engage with a convex outer surface of an femoral head prosthetic component.

According to another aspect, an orthopaedic system may comprise an acetabular cup prosthetic component including a concave curved inner surface, a femoral head prosthetic component including a convex curved outer surface configured to engage the concave curved inner surface of the acetabular cup prosthesis, an impactor head including an impaction surface that is configured to engage at least one of the concave curved inner surface of the acetabular cup prosthesis and the convex curved outer surface of the femoral head prosthetic component, and a suction cup coupled to the impactor head. The suction cup includes an outer rim positioned proximal of the impaction surface. The suction cup is configured to engage the at least one of the concave curved inner surface of the acetabular cup prosthesis and the convex curved outer surface of the femoral head prosthetic component to selectively couple the impactor head to the acetabular cup prosthesis and the femoral head prosthetic component.

In some embodiments, the impaction surface may be a first impaction surface configured to engage the concave curved inner surface of the acetabular cup prosthesis, and the impactor head may include a second impaction surface configured to engage the convex curved outer surface of the femoral head prosthetic component.

In some embodiments, the impactor head may be a first impactor head that is removably coupled to the suction cup. The impaction surface of the first impactor head may be configured to engage the concave curved inner surface of the acetabular cup prosthesis. The orthopaedic system may further comprise a second impactor head that is configured to be coupled to the suction cup in place of the first impactor head. The second impactor head may include an impaction surface that is configured to engage the convex curved outer surface of the femoral head prosthetic component.

In some embodiments, the suction cup may include an inner wall that extends distally from the proximal rim to define a cavity, and the impactor head may be positioned in the cavity of the suction cup. Additionally, in some embodiments, the inner wall may define at least one corrugation.

In some embodiments, the impactor head may include a proximal opening, and the suction cup may extend outwardly from the proximal opening.

According to another aspect, a method of performing an orthopaedic surgical procedure comprises positioning an impaction surgical instrument relative to an orthopaedic prosthetic component, aligning a suction cup positioned at the proximal end of the impaction surgical instrument with the orthopaedic prosthetic component, advancing the suction cup into engagement with the orthopaedic prosthetic component to couple the impaction surgical instrument to the orthopaedic prosthetic component, moving an impactor head of the impaction surgical instrument into engagement with the orthopaedic prosthetic component while the suction cup is engaged with the orthopaedic prosthetic component, and impacting the orthopaedic prosthetic component into its use position.

In some embodiments, positioning the impaction surgical instrument relative to the orthopaedic prosthetic component may include positioning the impaction surgical instrument relative to an acetabular cup prosthetic component, and impacting the orthopaedic prosthetic component into its use position may include driving the acetabular cup prosthetic component into a patient's acetabulum.

In some embodiments, aligning the suction cup positioned at the proximal end of the impaction surgical instrument with the orthopaedic prosthetic component may include aligning the suction cup with a concave inner surface of the acetabular cup prosthetic component.

In some embodiments, positioning the impaction surgical instrument relative to the orthopaedic prosthetic component may include positioning the impaction surgical instrument relative to an femoral head prosthetic component, and impacting the orthopaedic prosthetic component into its use position may include driving the femoral head prosthetic component onto a femoral stem prosthetic component.

In some embodiments, aligning the suction cup positioned at the proximal end of the impaction surgical instrument with the orthopaedic prosthetic component may include aligning the suction cup with a convex outer surface of the femoral head prosthetic component.

BRIEF DESCRIPTION OF THE DRAWINGS

The detailed description particularly refers to the following figures, in which:

FIG. 14 is a perspective view of another embodiment of an impaction tool of an orthopaedic surgical instrument; and FIG. 15 is a cross-sectional side elevation view taken along the line 15-15 in FIG. 14.

DETAILED DESCRIPTION OF THE DRAWINGS

Figure 1:
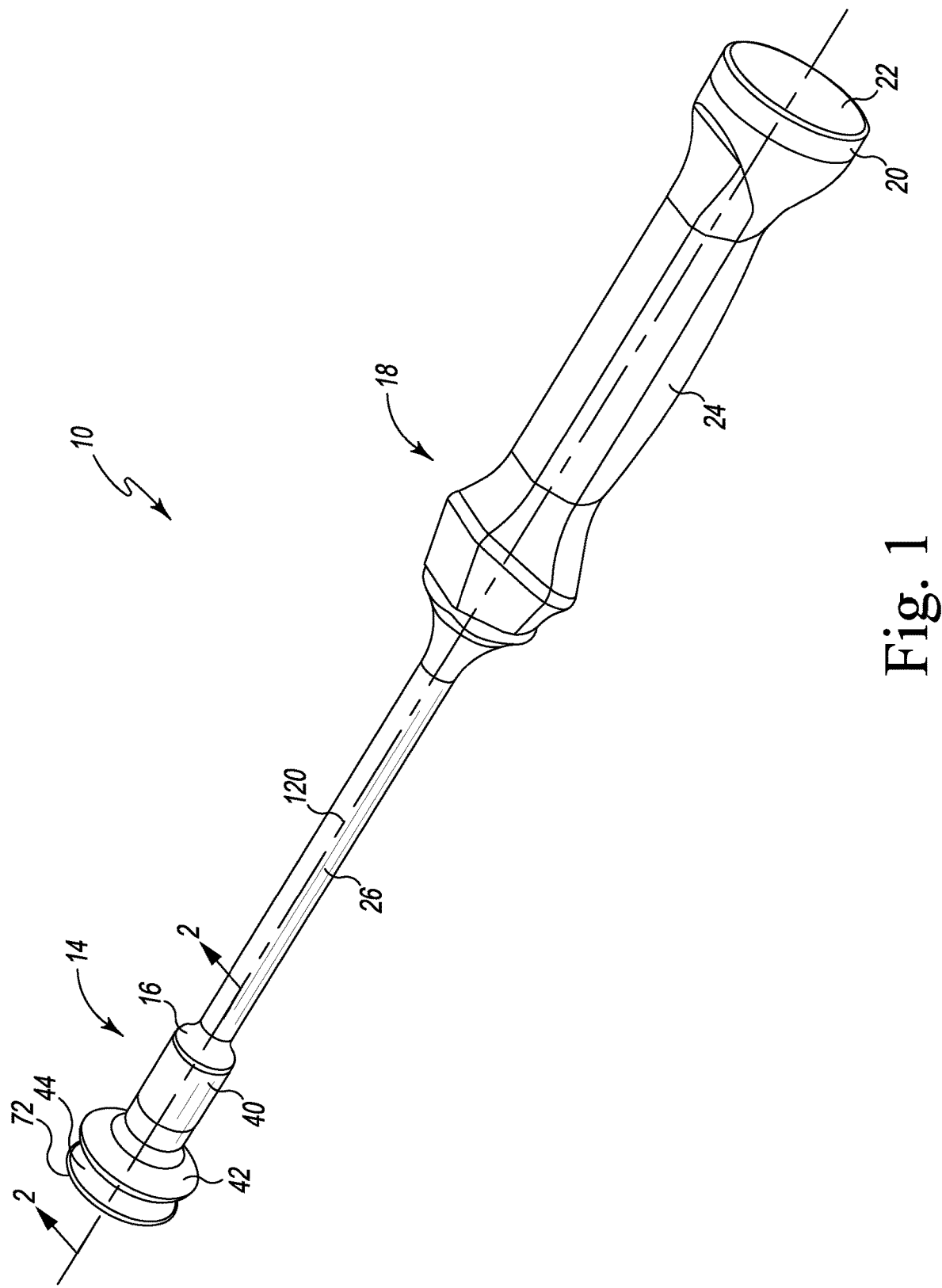
FIG. 1 is a perspective view of an orthopaedic surgical instrument.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout the specification in reference to the orthopaedic implants or prostheses and surgical instruments described herein as well as in reference to the patient's natural anatomy. Such terms have well-understood meanings in both the study of anatomy and the field of orthopaedics. Use of such anatomical reference terms in the written description and claims is intended to be consistent with their well-understood meanings unless noted otherwise.

Referring now to FIG. 1, an orthopaedic surgical instrument 10 configured for use during the implantation of a hip orthopaedic prosthesis assembly 12 (see FIG. 3) includes an impaction tool 14 secured to a proximal end 16 of an impaction handle 18. As described in greater detail below, the impaction tool 14 is configured to be attached to one or more components of the prosthesis assembly 12 to insert and then impact the component(s) into the patient's bone such that only a single instrument is needed to perform both the insertion step (i.e., the positioning of the implant in the joint space) and the impaction step (i.e., the impacting of the implant into the patient's bone).

The impaction handle 18 extends from the proximal end 16 to a distal end 20. In the illustrative embodiment, the distal end 20 has an strike plate 22 that is sized and shaped to be struck by a mallet or other surgical tool to impact the component(s) of the prosthesis assembly 12 into place in the patient's bone. The impaction handle 18 includes a grip 24 that extends proximally from the distal end 20 and is sized to be grasped by a hand of a surgeon or other user of the instrument 10. An elongated shaft 26 extends from the grip 24 to the proximal end 16.

Figure 2:
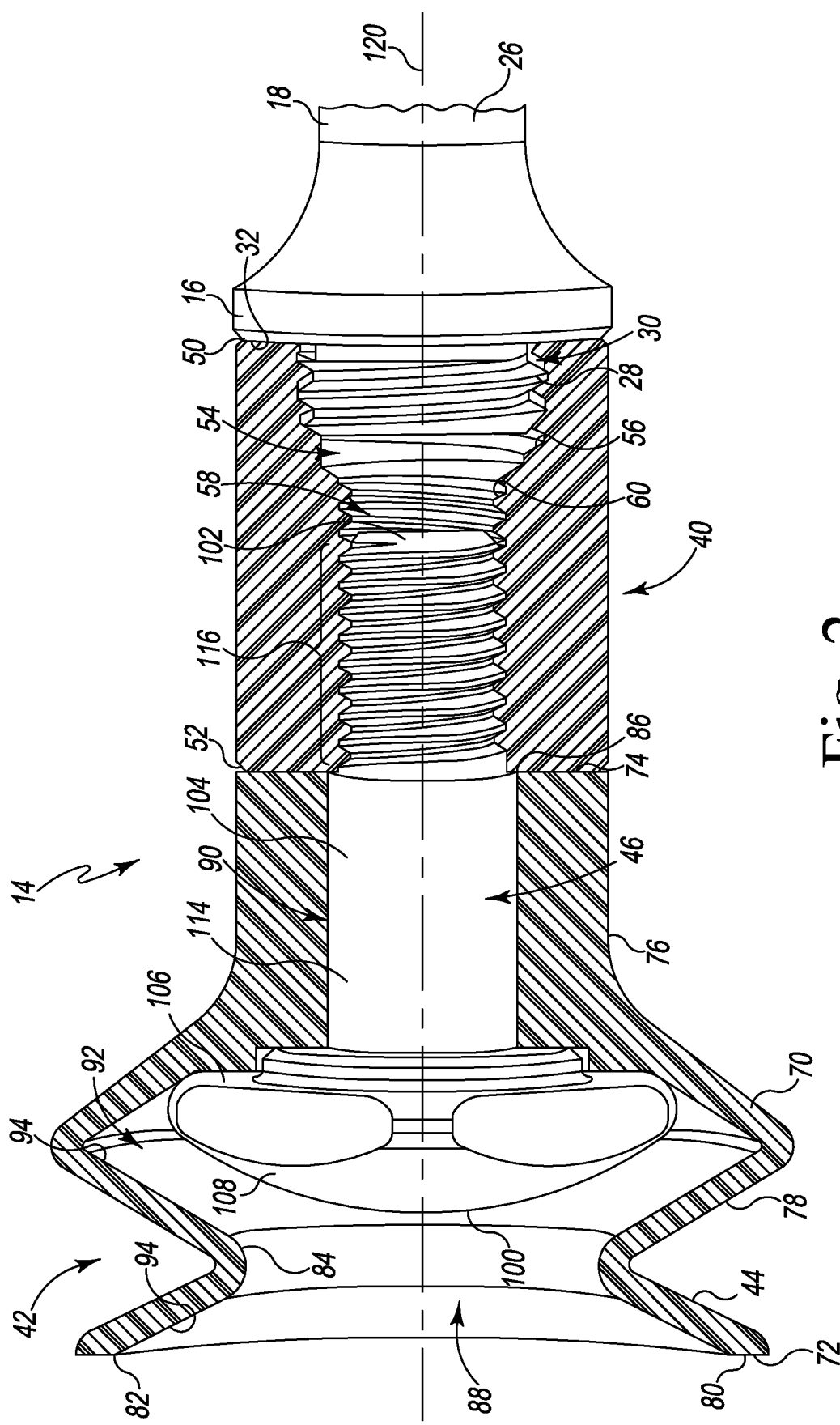
FIG. 2 is a cross-sectional elevation view of the impaction tool of the orthopaedic surgical instrument taken along the line 2-2 in FIG. 1.

As shown in FIG. 2, a threaded shank 28 is formed at the proximal end 16 of the impaction handle 18. In the illustrative embodiment, the shank 28 is sized to be received in a corresponding threaded bore 30 defined in the impaction tool 14 to secure the impaction tool 14 to the impaction handle 18. The shank 28 illustrative extends outwardly from a proximal surface 32 of the elongated shaft 26, which is shaped to engage the distal end of the impaction tool 14. It should be appreciated that in other embodiments the impaction tool may include the threaded shank and the impaction handle may include the threaded bore to secure the tool to the impaction handle. In still other embodiments, other means may be used to secure the impaction handle to the impaction tool. Instead of being modular, the impaction handle and the impaction tool may also be formed as a single, monolithic component.

The impaction tool 14 includes a connector body 40 that includes the threaded bore 30 and a proximal coupler 42 configured to secure the impaction tool 14 to the component(s) of the prosthesis assembly 12. In the illustrative embodiment, the proximal coupler 42 includes a suction cup 44 that uses negative pressure to adhere to the component of the prosthesis assembly 12 to secure the impaction tool 14 (and hence the impaction handle 18) to the prosthetic component. The suction cup 44 is formed from an elastomeric material such as, for example, rubber. In the illustrative embodiment, the connector body 40 is formed from a metallic material, such as stainless steel, which may be autoclaved and sterilized between surgical procedures such that the connector body 40 may be used in multiple procedures. It should be appreciated that in other embodiments the connector body 40 may be formed from a plastic material such as, for example, polyethylene.

As shown in FIG. 2, the tool 14 also includes an impactor head 46 that is positioned within the proximal coupler 42 and is secured to the connector body 40. The impactor head 46 is formed from a polymeric material such as, for example, polyethylene. In other embodiments, it may be formed from a metallic material such as, for example, stainless steel. Although the impaction tool 14 includes multiple, separate components, it should be appreciated that, for example, the impaction head and the connector body may be formed as a single, monolithic component.

The connector body 40 extends from a distal end 50 that abuts the proximal surface 32 of the elongated shaft 26 of the impaction handle 18 to a proximal end 52. In the illustrative embodiment, the body 40 has a cylindrical outer surface, but it should be appreciated that the body may take other geometric forms in other embodiments. A passageway 54 extends through the ends 50, 52. The distal section of the passageway 54 includes the threaded bore 30, which is defined by an inner wall 56 that includes a plurality of female threads shaped to engage the male threads of the threaded shank 28 of the impaction handle 18.

The proximal section of the passageway 54 includes another threaded bore 58 that opens into the threaded bore 30. An inner wall 60 extends inwardly from the proximal end 52 to define the threaded bore 58 in the connector body. The inner wall 60 includes additional female threads that are configured to engage corresponding male threads of the impactor head 46, as described in greater detail below. In the illustrative embodiment, the threaded bore 30 has a diameter that is larger than the diameter of the threaded bore 30 such that the connector body 40 may be attached to the impaction handle 18 in only a single orientation.

The suction cup 44 of the proximal coupler 42 includes an outer body 70 that extends from a proximal tip 72 to a distal end 74 that abuts the proximal end 52 of the connector body 40. The outer body 70 includes a cylindrical section 76 that extends proximally from the distal end 74 and a corrugated section 78 that extends from the cylindrical section 76 to the proximal tip 72. As shown in FIG. 2, the suction cup 44 has an outer rim 80 that defines a proximal opening 82 in the tip 72.

An inner wall 84 extends inwardly from the proximal opening 82 to a distal opening 86 defined in the distal end 74 of the cup outer body 70. The inner wall 84 and the openings 82, 86 cooperate to define a passageway 88 extending through the suction cup 44. The passageway 88 includes a distal bore 90 that extends from the opening 86 and opens into a proximal cavity 92 of the passageway 88. In the illustrative embodiment, the inner wall 84 of the suction cup 44 defines a plurality of corrugations 94 in the proximal cavity 92.

As shown in FIG. 2, the impactor head 46 extends from a proximal tip 100 that is positioned in the cavity 92 of the suction cup 44 to a distal end 102 that is configured to be attached to the connector body 40. The impactor head 46 includes an elongated body 104 that extends from the distal end 102 to a contact plate 106, which extends to the proximal tip 100. The contact plate 106 includes an impaction surface 108 that is sized and shaped to engage an acetabular cup prosthetic component 110 (see FIG. 3) of the prosthesis assembly 12. In the illustrative embodiment, the impaction surface 108 is a convex curved surface that is shaped to engage a corresponding concave curved surface 112 of the acetabular cup prosthetic component 110. The outer rim 80 of the suction cup 44 is positioned proximal of the impaction surface 108.

The elongated body 104 of the impactor head 46 includes a central section 114 that extends distally from the contact plate 106. The elongated body 104 also includes a plurality of male threads 116 that begin at the distal end 102 of the impactor head 46 and extend to the central section 114. In the illustrative embodiment, the male threads 116 are shaped to engage the corresponding female threads that define the threaded bore 58 of the connector body 40 to secure the impactor head 46 to the connector body 40. As shown in FIG. 2, the cylindrical section 76 of the suction cup 44 grips the central section 114 of the elongated body 104 to secure the suction cup 44 to the impactor head 46. It should be appreciated that the suction cup 44 may be pulled free of the impactor head 46 and discarded following the completion of a surgical procedure. A new suction cup may be attached to the impactor head after the impactor head has been sterilized.

As shown in FIGS. 1-2, the orthopaedic surgical instrument 10 has a longitudinal axis 120 that extends from the distal end 20 of the impaction handle 18 to the proximal tip 72 of the impaction tool 14. When a surgeon or other user hits the strike plate 22 of the impaction handle 18 with a mallet or other surgical tool, force is transferred along the axis 120 to the impaction surface 108 of the impactor head 46 to implant the prosthetic component (e.g., acetabular cup component 110). In the illustrative embodiment, the central section 114 of the elongated body 104 has a diameter that is larger than the diameter of the threaded bore 58. In that way, the central section 114 engages the proximal end 52 of the connector body 40 to transfer the force from the impaction handle 18 to the impaction surface 108 via the engagement between the connector body 40, the proximal surface 32 of the elongated shaft 26, and the central section 114 of the impactor head and not exclusively via the threaded connections.

Figure 3:
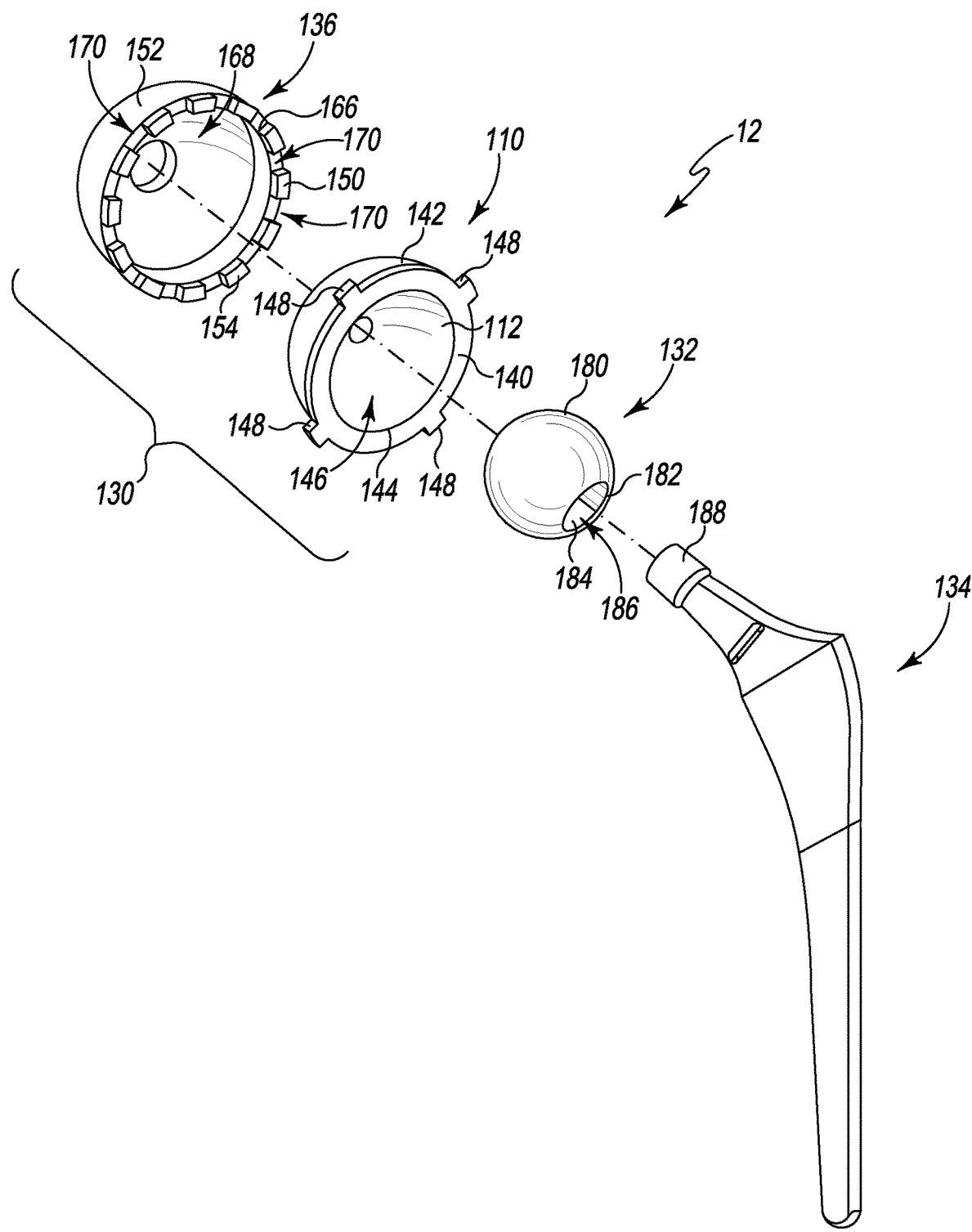
FIG. 3 is an exploded perspective view of a hip orthopaedic prosthesis assembly.

Referring now to FIG. 3, the hip orthopaedic prosthesis assembly 12 includes a plurality of components, including the acetabular cup prosthetic component 110. The components of the assembly 12 include an acetabular cup 130 that is configured to receive a femoral head component 132 of the assembly 12. The assembly 12 also includes a femoral stem component 134 that is configured to be secured to the femoral head component 132. In the illustrative embodiment, the acetabular cup 130 includes a shell 136 that is sized to be implanted in a surgically-prepared acetabulum of a patient's pelvis and the acetabular cup prosthetic component 110, which is a liner configured to be attached to the shell 136. The liner 110 is illustratively formed from a polymeric material such as, for example, polyethylene, and the shell 136 is separately formed from an implant-grade metallic material such as, for example, cobalt chromium.

The liner 110 includes a distal rim 140 and a convex outer surface 142 that extends from the rim 140. An opening 144 is defined by the distal rim, and, as described above, the liner 110 includes a concave curved surface 112, which extends inwardly from the opening 144 to define a cavity 146 that is sized to receive the femoral head component 132. In the illustrative embodiment, the liner 110 also includes a plurality of tabs 148 that extend outwardly from the convex outer surface 142.

The shell 136 of the acetabular cup 130 also includes a distal rim 150 and a convex outer surface 152 that extends from the rim 150. In the illustrative embodiment, the outer surface 152 is sized and shaped to engage the surgically-prepared acetabulum and is porous to promote bone ingrowth after implantation of the shell 136. An opening 154 is defined by the distal rim 150, and the shell 136 includes a concave curved surface 166 that defines a cavity 168 sized to receive the liner 110. A plurality of slots 170 are defined in the distal rim 150, and each slot 170 is sized to receive one of the tabs 148 of the liner 110. It should be appreciated that in other embodiments the tabs and slots may be omitted.

During a surgical procedure, the shell 136 of the acetabular cup 130 may be implanted into the patient's surgically-prepared acetabulum. To secure the liner 110 to the implant shell 136, the outer surface 142 of the liner 110 is aligned with the cavity 168 of the shell 136. As described in greater detail below, the liner 110 is then advanced into the cavity 168 of the shell 136 such that the convex outer surface 142 of the liner 110 engages the concave curved surface 112 of the shell 136. The liner 110 is then impacted into the shell 136 to assemble the acetabular cup 130 within the patient's surgically-prepared acetabulum.

The orthopaedic surgical instrument 10 may be used to secure the liner 110 to the shell 136 and thereby assemble the acetabular cup 130. It should be appreciated that the orthopaedic surgical instrument 10 may also be configured to impact and thereby implant the shell 136 into the patient's surgically-prepared acetabulum. In such embodiments, the orthopaedic surgical instrument 10 may include a plurality of impaction tools 14 configured to be selectively and separately coupled to the impaction handle 18. Each impaction tool may be sized and shaped to engage a different component of the acetabular cup. Additionally, the liner and the shell may be included in a kit including liners and shells of different sizes to accommodate a variety of patient sizes.

In such embodiments, a surgical instrument system including a number of impaction tools having sizes and shapes to accommodate the different sizes of liners and shells may be provided.

Figure 4:
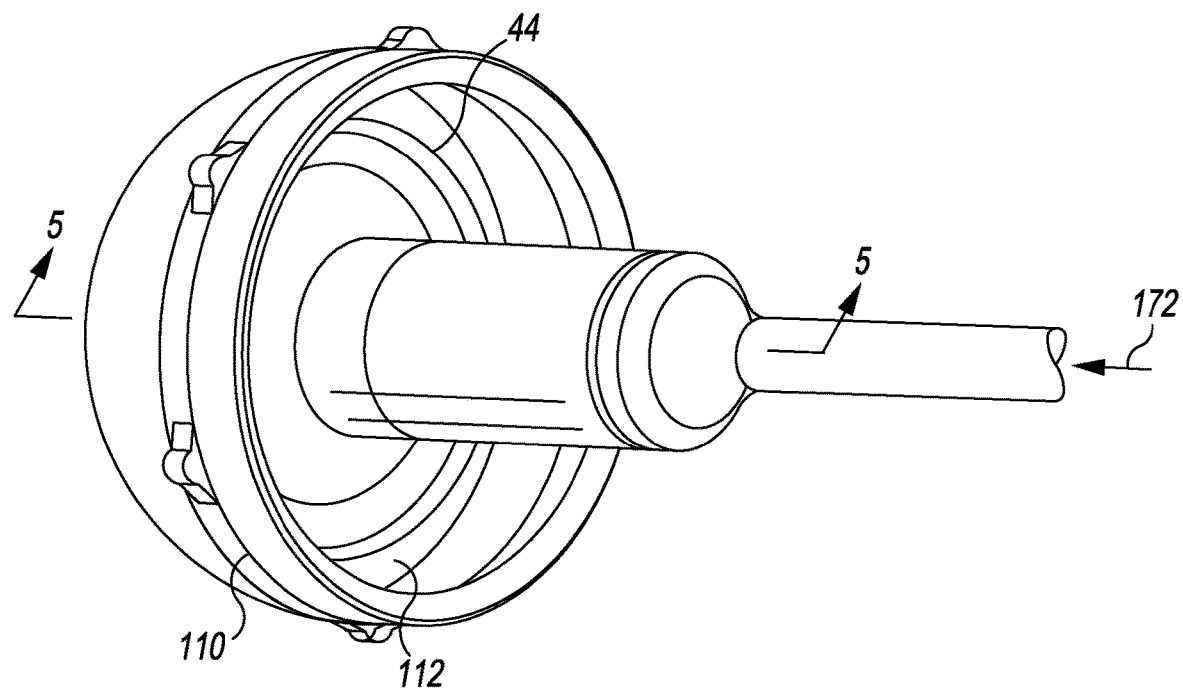
FIG. 4 is a perspective view of the impaction tool of the orthopaedic surgical instrument of FIG. 1 attached to an acetabular cup prosthetic component of the orthopaedic prosthesis assembly of FIG. 3.
Figure 5:
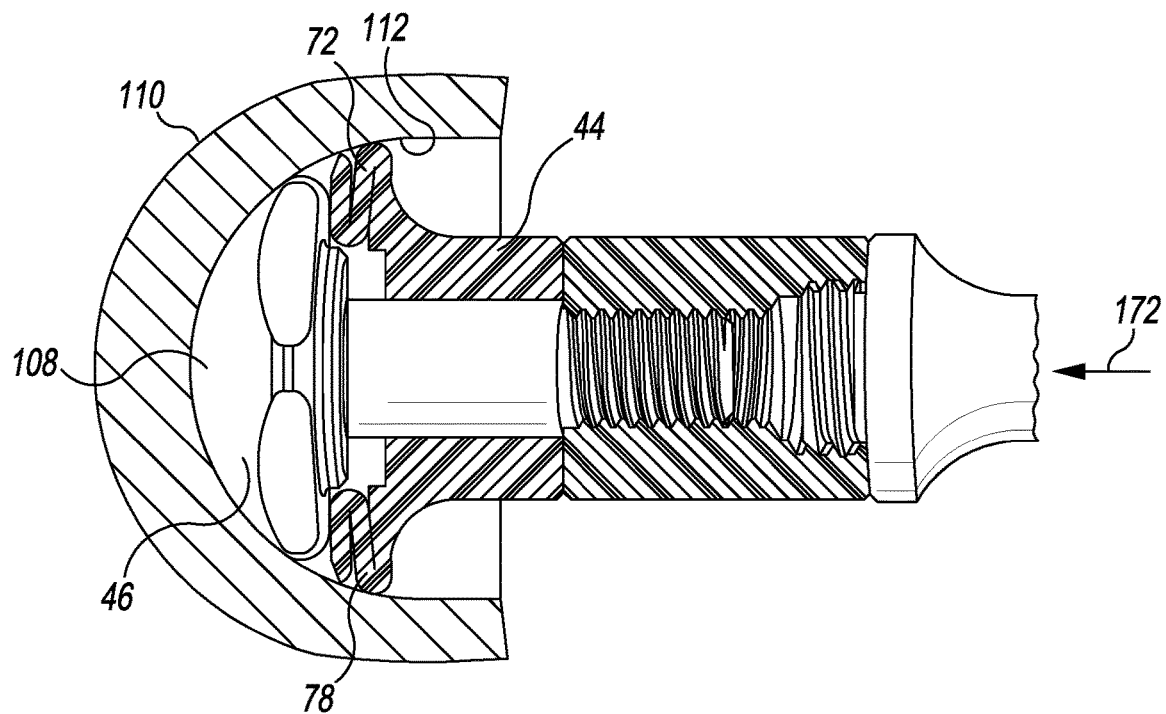
FIG. 5 is a cross-sectional elevation view taken along the line 5-5 in FIG. 4.
Figure 6:
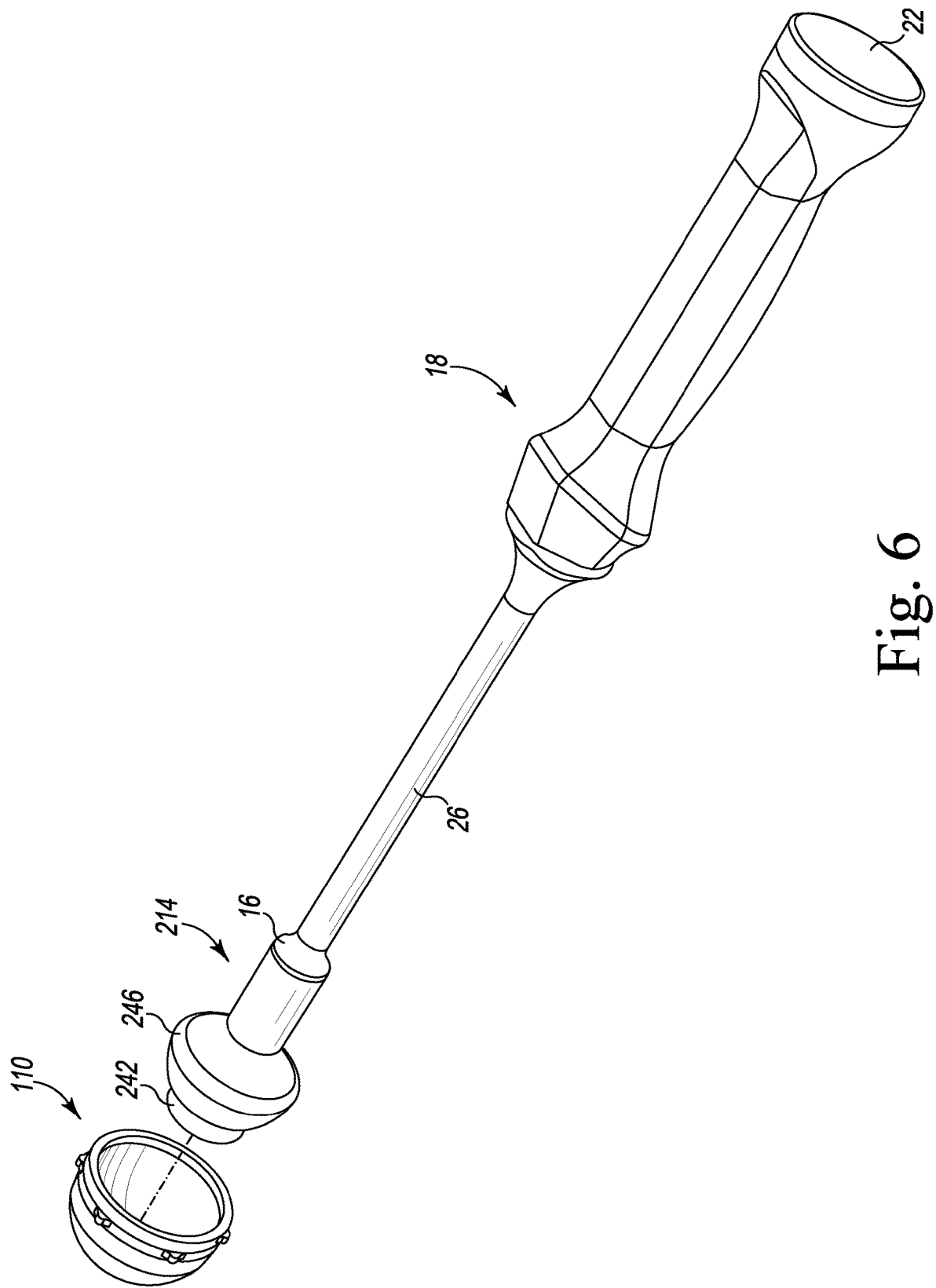
FIG. 6 is a perspective view of another embodiment of an impaction tool aligned with the acetabular cup prosthetic component of the orthopaedic prosthesis assembly of FIG. 3.

Referring now to FIGS. 4-5, the proximal tip 72 of the impaction tool 14 is sized to be positioned in the cavity 146 of the acetabular liner 110. To secure the impaction tool 14 to the liner 110, the proximal tip 72 is advanced in the direction indicated by arrow 172 in FIGS. 4-5 into engagement with the concave curved surface 112 of the liner 110. As the outer rim 80 of the suction cup 44 engages the concave curved surface 112, the corrugated section 78 of the suction cup 44 compresses and the impactor head 46 advances toward the curved surface 112. The compression of the corrugated section 78 expels air within the cavity 92 out along the rim 80, thereby creating a partial vacuum within the cavity 92 to secure the impaction tool 14 (and hence the handle 18) to the acetabular liner 110. As shown in FIG. 5, when the impaction surface 108 engages the concave curved inner surface 112 of the liner 110, the corrugated section 78 is almost fully compressed. The surgeon or other user may then use the impaction handle 18 to align the liner 110 with the acetabular shell 136 and advance the liner 110 into engagement with the shell 136. With the impaction surface 108 engaged with the liner 110, the surgeon may strike the plate 22 of the handle 18 to impact the liner 110 into the shell 136 to implant the liner 110 in the patient's bone.

As described above, the hip orthopaedic prosthesis assembly 12 also includes a femoral head component 132 that is configured to be secured to a femoral stem component 134. As shown in FIG. 3, the head component 132 includes a convex curved outer surface 180 that is configured to articulate with the concave curved inner surface 112 of the acetabular liner 110. The head component 132 includes a distal opening 182 and a tapered inner wall 184 that extends inwardly from the opening 182 to define an aperture 186 in the head component 132. The femoral stem component 134 includes a tapered trunnion 188 that is sized to be received in the aperture 186. In the illustrative embodiment, a taper lock secures the femoral head component 132 to the femoral stem component 134.

The impactor head of the orthopaedic surgical instrument 10 may be replaced with a femoral impactor head including a concave impaction surface sized to engage the convex curved outer surface 180 of the head component 132. In such embodiments, the suction cup may be de-attached from the impactor head 46 and attached to the femoral impactor head. The orthopaedic surgical instrument may then be used to impact the femoral head component 132 on to the stem component 134 to create the taper lock. The impactor heads may be included in an instrument system including a plurality of impactor heads. Additionally, each impactor head may be attached to a different impaction tool that are each configured to be selectively coupled to the handle 18.

Figure 7:
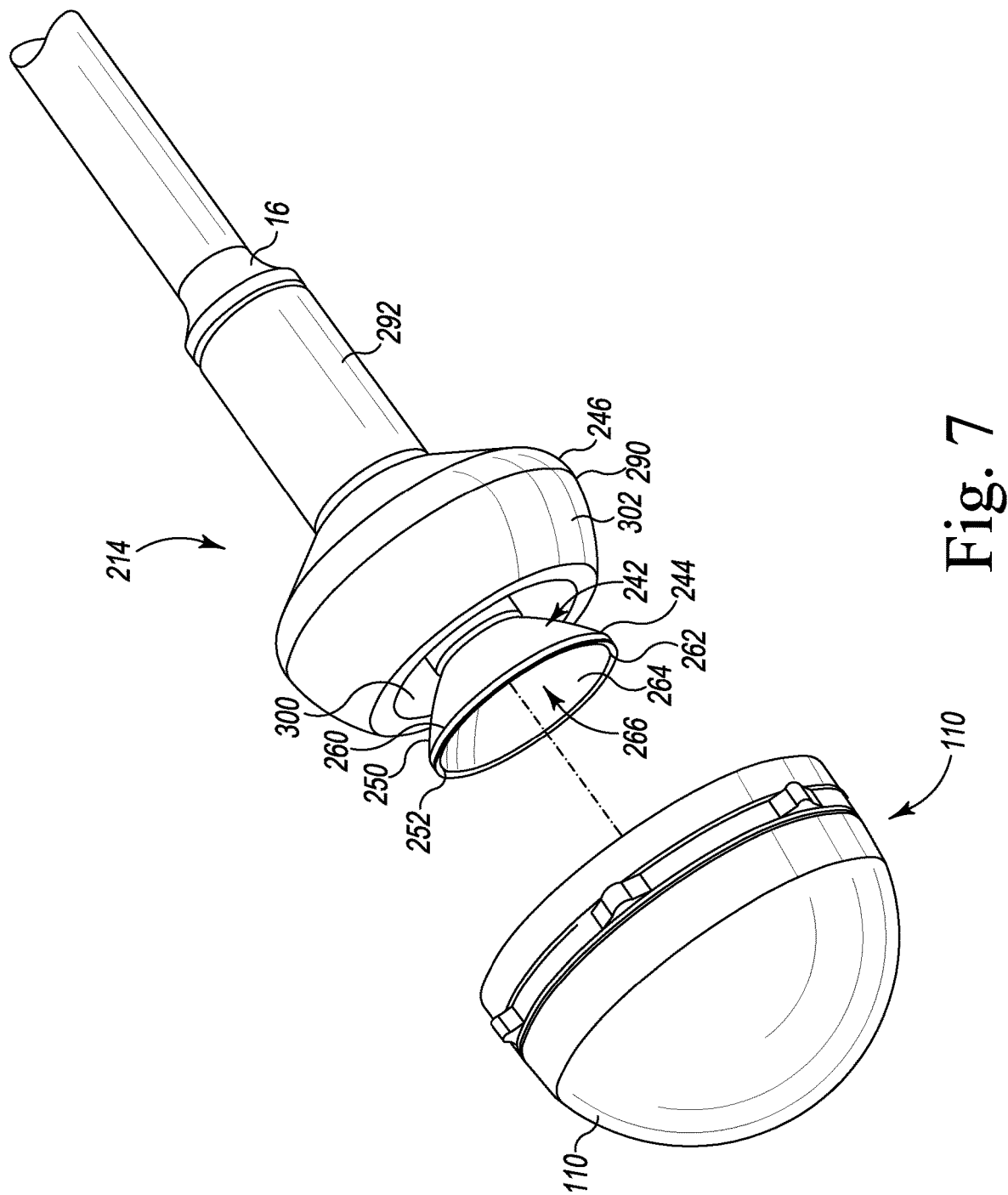
FIG. 7 is another perspective view of the impaction tool of FIG. 6 and the acetabular cup prosthetic component.
Figure 8:
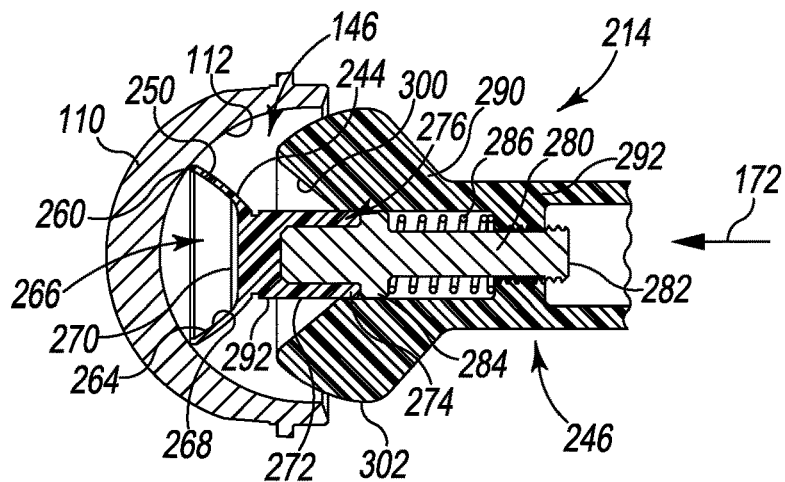
FIGS. 8-10 are cross-sectional side elevation views of a process for securing the acetabular cup prosthetic component to the impaction tool of FIG. 6.
Figure 9:
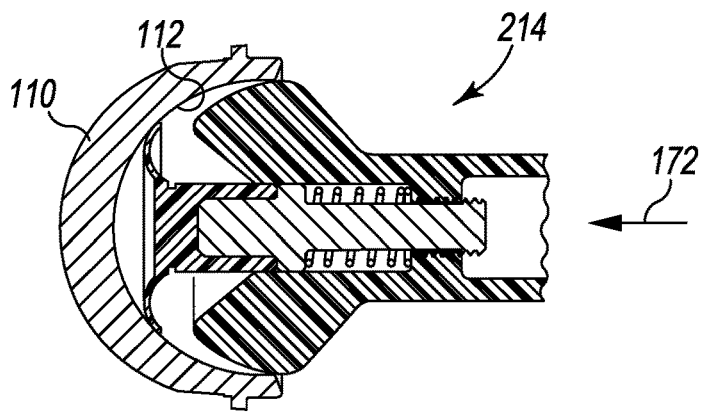
Figure 10:
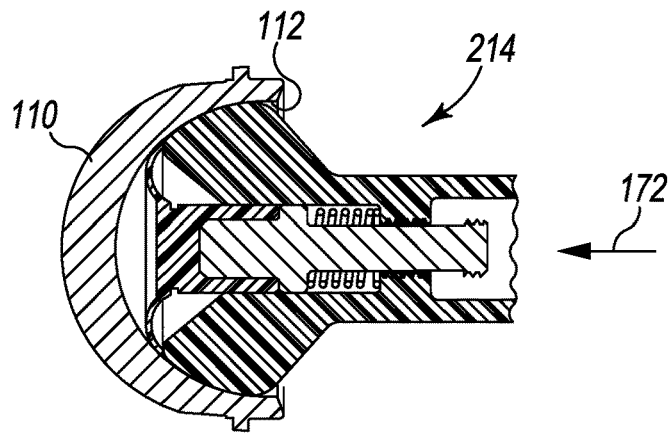
Figure 11:
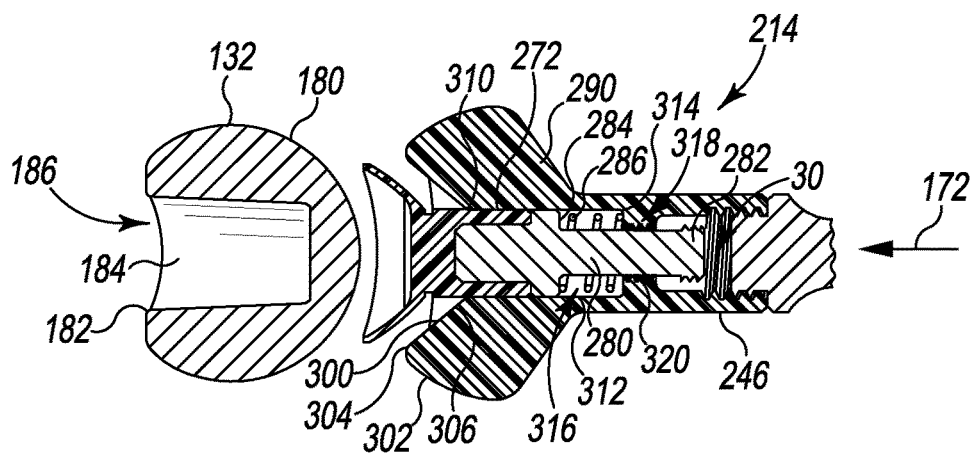
FIGS. 11-13 are cross-sectional side elevation views of a process for securing a femoral head prosthetic component of the orthopaedic prosthesis assembly of FIG. 3 to the impaction tool of FIG. 6.
Figure 12:
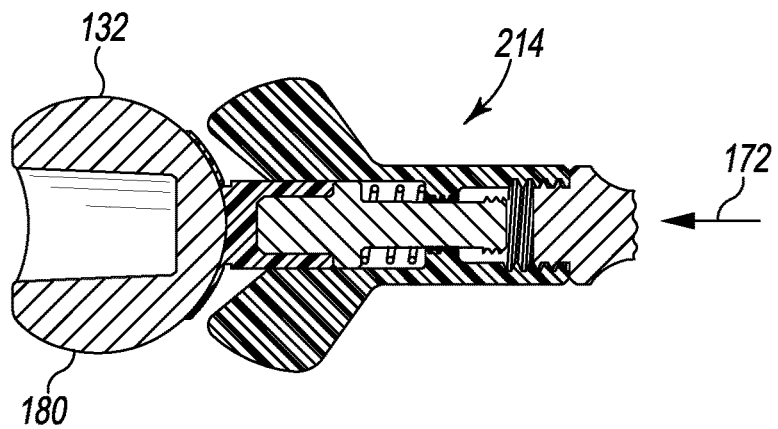
Figure 13:
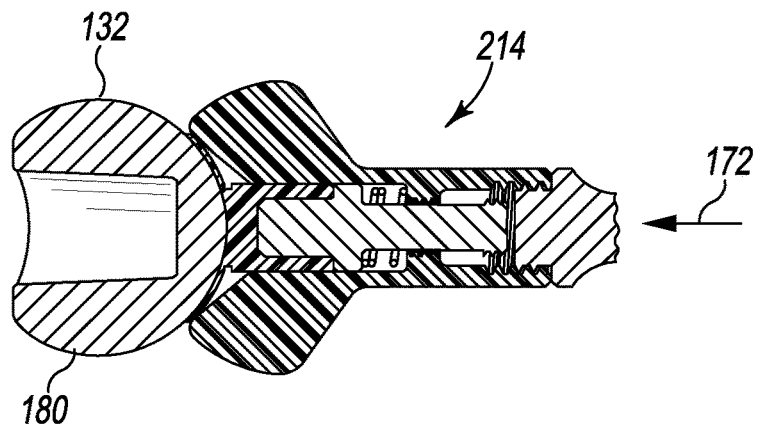

Referring now to FIGS. 6-13, another embodiment of an impaction tool (hereinafter impaction tool 214) configured to be coupled to the impaction handle 18 is shown. The impaction tool 214, like the impaction tool 14, includes a proximal coupler 242 configured to secure the impaction tool 214 to the components of the prosthesis assembly 12 and an impactor head 246 that is configured to impact the components into position. In the illustrative embodiment, the impaction tool 214 may be used to insert and impact the acetabular liner 110 (as shown in FIGS. 8-10) or the femoral head component 132 (as shown in FIGS. 11-13), as described in greater detail below.

In the illustrative embodiment, the proximal coupler 242 includes a suction cup 244 that uses negative pressure to adhere to the components of the prosthesis assembly 12 to secure the impaction tool 14 (and hence the impaction handle 18) to the prosthetic components. As shown in FIG. 7, the suction cup 244 includes a proximal flange 250 that extends from a proximal tip 252. An outer rim 260 of the proximal flange 250 defines a proximal opening 262 in the tip 252, and an inner wall 264 extends inwardly from the opening 262 to define a cavity 266 in the suction cup 244. As shown in FIG. 8, the inner wall 264 includes a concave curved inner surface 268 that extends from the opening 262 to a planar base surface 270.

The suction cup 244 also includes a main body 272 that extends distally from the flange 250 to a distal end 274 positioned in the impactor head 246. In the illustrative embodiment, an aperture 276 extends inwardly from the distal end 274, and the impaction tool 214 includes an elongated shaft 280 that is received in the aperture 276. The shaft 280 extends outwardly from the aperture 276 to a distal end 282. As shown in FIG. 8, the distal end 282 is threaded. An annular flange 284 extends outwardly from the shaft 280; as described in greater detail below, the flange 284 defines a seat for the spring 286.

The suction cup 244 is formed from an elastomeric material such as, for example, rubber, which grips the shaft 280 to secure the cup 244 to the shaft 280. The shaft 280 is illustratively formed from a plastic material such as, for example, polyethylene, but it should be appreciated that it may be formed from a metallic material such as stainless steel, which may be autoclaved and sterilized between surgical procedures. It should be appreciated that, for example, the elongated shaft and the suction cup may be formed as a single, monolithic component.

The impactor head 246 includes a contact body 290 and an elongated shaft 292 that extends distally from the contact body 290. The elongated shaft 292, like the connector body 40 described above, includes a threaded bore 30 that engages the threaded shank 28 of the impaction handle 18 to secure the impactor head 246 to the impaction tool 214. In the illustrative embodiment, the contact body 290 has an inner impaction surface 300 that is shaped to engage the convex outer surface 180 of the femoral head component 132 and an outer impaction surface 302 that is shaped to engage the concave inner surface 112 of the acetabular liner 110. The impactor head 246 is formed from a polymeric material such as, for example, polyethylene. In other embodiments, it may be formed from a metallic material such as, for example, stainless steel.

As shown in FIG. 11, the inner impaction surface 300 extends inwardly from a proximal opening 304 defined in the contact body 290. In the illustrative embodiment, the inner impaction surface 300 is a conical surface, but it should be appreciated that in other embodiments the impaction surface may have a curvature that matches the curvature of the femoral head component 132. The inner impaction surface 300 extends inwardly to an edge 306 that surrounds an inner opening 310 in the contact body 290.

An inner wall 312 extends inwardly from the opening 310 to a base wall 314. The base wall 314 cooperates with the inner wall 312 to define a passageway 316 in the impactor head 246. A through-hole 318 extends through the base wall 314 to connect the passageway 316 to the threaded bore 30. As shown in FIG. 11, a threaded inner wall 320 defines the through hole 318 in the illustrative embodiment.

The passageway 316 is sized to receive the main body 272 of the suction cup 244 and the elongated shaft 280 extends along the passageway 316 and through the hole 318 such that the distal end 282 of the shaft 280 is positioned in the proximal end of the threaded bore 30. The threaded inner wall 320 of the impactor head 246 is shaped to engage the threads defined on the distal end 282 of the shaft 280. In that way, after the distal end 282 of the shaft 280 has been advanced into the threaded bore 30, the distal end 282 is retained in the bore 30.

As described above, the impaction tool 214 includes a spring 286, which is positioned between the annular flange 284 and the base wall 314 of the impactor head 246. In the illustrative embodiment, the spring 286 is configured to bias the suction cup 244 outward from the impactor head 246, as shown in FIGS. 8-9 and 11-12, such that the suction cup 244 is advanced into contact with the selected prosthetic component before the impactor head 246. As shown in FIG. 8, for example, the spring biases the suction cup in an outward position in which the outer rim of the suction cup is a first distance from the proximal end of the impactor head. As shown in FIG. 9, the spring may be compressed such that a second, shorter distance is defined between the outer rim of the suction cup and the proximal end of the impactor head.

Referring now to FIGS. 8-10, the impactor head 246 is sized to be positioned in the cavity 146 of the acetabular liner 110. To secure the impaction tool 214 to the liner 110, the impactor head 246 and the suction cup 244 are advanced in the direction indicated by arrow 172 in FIGS. 8-10 into engagement with the concave curved surface 112 of the liner 110. As the outer rim 260 of the suction cup 244 engages the concave curved surface 112, the cup flange 250 peels backward to compress the cup 244 and the impactor head 246 advances into toward the curved surface 112. The compression of the cup 244 expels air within the cup cavity 266 out along the rim 260, thereby creating a partial vacuum within the cavity 266 to secure the impaction tool 214 (and hence the handle 18) to the acetabular liner 110. The surgeon or other user may then use the impaction handle 18 to align the liner 110 with the acetabular shell 136 and advance the liner 110 into engagement with the shell 136. With the impaction surface 302 engaged with the liner 110 as shown in FIG. 10, the surgeon may strike the plate 22 of the handle 18 to impact the liner 110 into the shell 136 to implant the liner 110 in the patient's bone.

Referring now to FIGS. 11-13, the inner impaction surface 300 of the impactor head 246 is sized to receive the femoral head component 132. To secure the impaction tool 214 to the femoral head component 132, the impactor head 246 and the suction cup 244 are advanced in the direction indicated by arrow 172 in FIGS. 11-13 into engagement with the convex curved surface 180 of the head component 132. As shown in FIG. 12, the cup flange 250 engages the head component 132, thereby creating a partial vacuum within the cavity 266 to secure the impaction tool 214 (and hence the handle 18) to the head component 132. The surgeon or other user may then use the impaction handle 18 to align the head component 132 with the trunnion 188 of the femoral stem component 134 and advance the head component 132 into engagement with the femoral stem component 134. With the impaction surface 302 engaged with the head component 132 as shown in FIG. 13, the surgeon may strike the plate 22 of the handle 18 to impact the head component 132 onto the femoral stem component 134 to secure the head component 132 to the stem component 134.

Referring now to FIGS. 14-15, another embodiment of an impaction tool (hereinafter impaction tool 414) configured to be coupled to the impaction handle 18 is shown. Similar to the impaction tool 214, the impaction tool 414 includes an inner impaction surface 300 that is shaped to engage the convex outer surface 180 of the femoral head component 132 and an outer impaction surface 302 that is shaped to engage the concave inner surface 112 of the acetabular liner 110. In that way, the impaction tool 414 may be used to insert and impact the acetabular liner 110 or the femoral head component 132, as described in greater detail below.

The impaction tool 414 includes a detachable suction cup 444 that is secured to a mounting pin 448 of the impactor head 446. The suction cup 444 includes an outer body 470 that extends from a proximal tip 472 to a distal end 474 that is mounted on the pin 448. The outer body 470 includes a cylindrical section 476 that extends distally from the distal end 474 and a corrugated section 478 that extends from the cylindrical section 476 to the proximal tip 472. As shown in FIG. 15, the suction cup 444 has an outer rim 480 that defines a proximal opening 482 in the tip 472.

An inner wall 484 extends inwardly from the proximal opening 482 to a distal opening 486 defined in the distal end 474 of the cup outer body 470. The inner wall 484 and the openings 482, 486 cooperate to define a passageway 488 extending through the suction cup 444. The passageway 488 includes a distal bore 490 that extends from the opening 486 and is sized to receive the mounting pin 448. The bore 490 opens into a proximal cavity 492 of the passageway 488. In the illustrative embodiment, the inner wall 484 of the suction cup 444 defines a plurality of corrugations 494 in the proximal cavity 492. Similar to the embodiment of FIGS. 1-2, the corrugations 494 are configured to compress to a partial vacuum within the cavity 492 to secure the impaction tool 14 (and hence the handle 18) to the selected prosthetic component.

In the embodiment of FIGS. 14-15, the position of the suction cup 444 relative to the impactor head 446 is adjustable. As shown in FIG. 15, mounting pin 448 is coupled to an adjustable bushing 500 that is positioned in a passageway 502 defined in the impactor head 446. The bushing 500 is threaded into the passageway 502 such that it may be moved toward and away from the inner impaction surface 300 and thereby change the position of the suction cup relative to the impactor head.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the method, apparatus, and system described herein. It will be noted that alternative embodiments of the method, apparatus, and system of the present disclosure may not include all of the features described yet still benefit from at least some of the advantages of such features. Those of ordinary skill in the art may readily devise their own implementations of the method, apparatus, and system that incorporate one or more of the features of the present invention and fall within the spirit and scope of the present disclosure as defined by the appended claims.

The invention claimed is:

1. An orthopaedic surgical instrument, comprising:
    a first impactor head having a convex curved impaction surface configured to engage a concave curved surface of an acetabular cup prosthesis,
    a second impactor head having a concave curved impaction surface configured to engage a convex curved surface of a femoral head prosthesis, and
    a suction cup configured to be selectively coupled to the first impactor head and the second impactor head, the suction cup including a distal opening that is defined by an outer rim positioned proximal of the impaction surface of the first impactor head or the second impactor head when one of the impactor heads is coupled to the suction cup,
    wherein the suction cup is configured to engage both the concave curved surface of the acetabular cup prosthesis and the convex curved surface of the femoral head prosthesis so as to selectively couple the first impactor head to the to the acetabular cup prosthesis and the second impactor head to the femoral head prosthesis.

2. The orthopaedic surgical instrument of claim 1, wherein:
    the suction cup includes an inner wall that extends distally from the proximal opening to define a cavity, and
    the impaction surface of the first impactor head or the second impactor head is positioned in the cavity of the suction cup when one of the impactor heads is coupled to the suction cup.

3. The orthopaedic surgical instrument of claim 2, wherein the inner wall defines at least one corrugation.

4. The orthopaedic surgical instrument of claim 1, wherein the suction cup includes an outer body that extends from the outer rim to a distal end, and the outer body surrounds the the first impactor head or the second impactor head when one of the impactor heads is coupled to the suction cup.

5. The orthopaedic surgical instrument of claim 1, further comprising an elongated body that is coupled to one of the first impactor head or the second impactor head and the suction cup, the elongated body including a handle configured to be gripped by a user and an impaction plate.

6. The orthopaedic surgical instrument of claim 5, wherein the elongated body is removably coupled to one of the first impactor head or the second impactor head and the suction cup.

* * * * *